(12) United States Patent
Suzuki (10) Patent No.: US 10,159,442 B2
(45) Date of Patent: Dec. 25, 2018

(54) PHYSIOLOGICAL INFORMATION PROCESSING SYSTEM

(71) Applicant: NIHON KOHDEN CORPORATION, Shinjuku-Ku, Tokyo (JP)

(72) Inventor: Tetsuo Suzuki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 225 days.

(21) Appl. No.: 15/281,290

(22) Filed: Sep. 30, 2016

(65) Prior Publication Data
US 2017/0100077 A1    Apr. 13, 2017

(30) Foreign Application Priority Data

Oct. 9, 2015    (JP) ................ 2015-2009258

(51) Int. Cl.
| | | |
|---|---|---|
| A61B 5/00 | (2006.01) | |
| A61B 5/024 | (2006.01) | |
| A61B 5/0476 | (2006.01) | |
| A61B 5/1455 | (2006.01) | |

(Continued)

(52) U.S. Cl.
CPC .............. *A61B 5/72* (2013.01); *A61B 5/0006* (2013.01); *A61B 5/02416* (2013.01); *A61B 5/0402* (2013.01); *A61B 5/0476* (2013.01); *A61B 5/14551* (2013.01); *A61B 5/6801* (2013.01); *A61B 5/7203* (2013.01); *A61B 5/0428* (2013.01); *A61B 2562/227* (2013.01)

(58) Field of Classification Search
CPC ....... A61B 5/72; A61B 5/006; A61B 5/02416; A61B 5/0402; A61B 5/0476; A61B 5/14551; A61B 5/6801; A61B 5/7203; A61B 5/0428; A61B 2562/227

See application file for complete search history.

(56) References Cited

U.S. PATENT DOCUMENTS 6,462,766 B1 *  10/2002  Roeber ............ B41J 2/37
                                            347/190
2005/0101875 A1 *  5/2005  Semler ............ A61B 5/04085
                                            600/509

(Continued)

OTHER PUBLICATIONS

Anonymous, "Welch Allyn® 1500 Patient Monitor", Welch Allyn, 2010 (retrieved on the internet on Oct. 9, 2015), 100 pages total, intl.welchallyn.com/documents/Patient%20Monitoring/Continuous%20Monitoring/1500/DFU_ENG_1500PatientMonitor.pdf.

*Primary Examiner* — Manuel L Barbee
(74) *Attorney, Agent, or Firm* — Sughrue Mion, PLLC (57) ABSTRACT

First and second sensors attached to a living body are connected to first and second input connectors respectively. An analog-to-digital converter converts a first analog voltage signal input from the first sensor through the first input connector into a first digital voltage signal. A first voltage-to-current converter converts the first digital voltage signal into a first analog current signal. A first interface connector outputs a second analog voltage signal and the first analog current signal, the second analog voltage signal being input from the second sensor through the second input connector. A physiological information processing apparatus has a second interface connector through which the first analog current signal and the second analog voltage signal are input to the physiological information processing apparatus.

11 Claims, 8 Drawing Sheets

(51) Int. Cl.
*A61B 5/0402* (2006.01)
*A61B 5/0428* (2006.01)

(56) References Cited

U.S. PATENT DOCUMENTS

| | | | | |
|---|---|---|---|---|
| 2006/0009688 A1* | 1/2006 | Lamego | A61B 5/14551 | |
| | | | | 600/323 |
| 2010/0331716 A1* | 12/2010 | Watson | A61B 5/02416 | |
| | | | | 600/538 |
| 2011/0209915 A1* | 9/2011 | Telfort | A61B 5/04282 | |
| | | | | 174/71 R |
| 2014/0257119 A1* | 9/2014 | Lemay | A61B 5/6844 | |
| | | | | 600/509 |

* cited by examiner

FIG. 8

PHYSIOLOGICAL INFORMATION PROCESSING SYSTEM

CROSS-REFERENCE TO RELATED APPLICATION(S)

The present application claims priority from Japanese Patent Application No. 2015-200928 filed on Oct. 9, 2015, the entire content of which is incorporated herein by reference.

BACKGROUND

The presently disclosed subject matter relates to a system for processing physiological information acquired through sensors attached to a living body.

A related art system includes a physiological information processing apparatus such as a bedside monitor. The bedside monitor may be, for example, the one disclosed in "Welch Allyn 1500 Patient Monitor", Welch Allyn, retrieved on Oct. 9, 2015 at intl.welchallyn.com/documents/Patient%20Monitoring/Continuous%20Monitoring/1500/DFU_ENG_1500PatientMonitor.pdf. Signals output from sensors attached to a living body are input to the bedside monitor. The bedside monitor processes the signals and presents physiological information to a user. The bedside monitor includes a connector for analog signal input and a connector for digital signal input independently. An analog signal output from one of the sensors attached to the living body is input to the analog signal input connector. A digital signal output from another sensor attached to the living body or a digital signal obtained by analog-to-digital conversion of an analog signal output from the sensor is input to the digital signal input connector.

SUMMARY

There is a demand for an integration of the digital signal connector with the analog signal connector, mainly for the purpose of downsizing and cost reduction of the bedside monitor. However, since digital signal communication is communication based on a change in voltage, noise caused by space capacitive coupling is apt to be mixed into an analog signal communication path. To avoid such a noise mixture, for example, a shield for protecting the analog signal path from the noise may be provided inside the connector and/or a digital signal path and the analog signal path may be arranged so as to be separated from each other as much as possible. However, such measures would increase the size and cost of the connector, and it would be difficult to achieve the purpose of downsizing and cost reduction of the bedside monitor.

Illustrative aspects of the presently disclosed subject matter suppress an increase in the size or cost of a physiological information processing apparatus such as a bedside monitor while avoiding mixture of noise into signal communication.

According to a first aspect of the presently disclosed subject matter, a physiological information processing system includes a first input connector to which a first sensor to be attached to a living body is connected, a second input connector to which a second sensor to be attached to the living body is connected, an analog-to-digital converter configured to convert a first analog voltage signal into a first digital voltage signal, the first analog voltage signal being input from the first sensor through the first input connector, a first voltage-to-current converter configured converts the first digital voltage signal into a first analog current signal, a first interface connector configured to output a second analog voltage signal and the first analog current signal, the second analog voltage signal being input from the second sensor through the second input connector, a physiological information processing apparatus having a second interface connector through which the first analog current signal and the second analog voltage signal are input to the physiological information processing apparatus, a first signal processor provided inside the physiological information processing apparatus to convert the first analog current signal into a first physiological information signal, and a second signal processor provided inside the physiological information processing apparatus to convert the second analog voltage signal into a second physiological information signal, the second physiological information signal being a digital voltage signal.

According to a second aspect of the presently disclosed subject matter, a physiological information processing system includes a first input terminal configured to receive a first signal, the first signal being an analog signal, a second input terminal configured to receive a second signal, the second signal being an analog signal, a switch configured to output one of the first signal and the second signal as an analog output signal, a first interface connector configured to output the analog output signal, a physiological information processing apparatus having a second interface connector through which the analog output signal is input to the physiological information processing apparatus, a signal processor provided inside the physiological information processing apparatus to convert the analog output signal into a physiological information signal, a signal selector provided inside the physiological information processing apparatus to output a first selection signal to select one of the first signal and the second signal, the first selection signal being a digital voltage signal, a voltage-to-current converter provided inside the physiological information processing apparatus to convert the first selection signal into an analog current signal and to output the analog current signal from the second interface connector, and a current-to-voltage converter configured to convert the analog current signal into a second selection signal, the analog current signal being input through the first interface connector, and the second selection signal being a digital voltage signal. The switch selects one of the first signal and the second signal based on the second selection signal.

According to a third aspect of the presently disclosed subject matter, a physiological information processing system includes a first output terminal configured to be electrically connected to a first device of a sensor attached to a living body, a second output terminal configured to be electrically connected to a second device of the sensor, a physiological information processing apparatus having a first interface connector, a device driving section provided inside the physiological information processing apparatus to output a device driving signal from the first interface connector, the device driving signal being an analog signal that drives the first device and the second device, a second interface connector configured to receive the device driving signal, a switch configured to output the device driving signal from one of the first output terminal and the second output terminal, the device driving signal being input from the second interface connector, a signal selector provided inside the physiological information processing apparatus to output a first selection signal, the selection signal being a digital voltage signal, a voltage-to-current converter provided inside the physiological information processing apparatus to convert the first selection signal into an analog current signal and to output the analog current signal from the first interface connector, and a current-to-voltage converter configured to convert the analog current signal into a second selection signal, the analog current signal being input through the second interface connector, and the second selection signal being a digital voltage signal. The switch selects one of the first output terminal and the second output terminal based on the second selection signal.

DETAILED DESCRIPTION

Hereinafter, exemplary embodiments of the presently disclosed subject matter will be described in detail with reference to the accompanying drawings. The drawings may not be to scale for the purpose of illustration.

Figure 1:
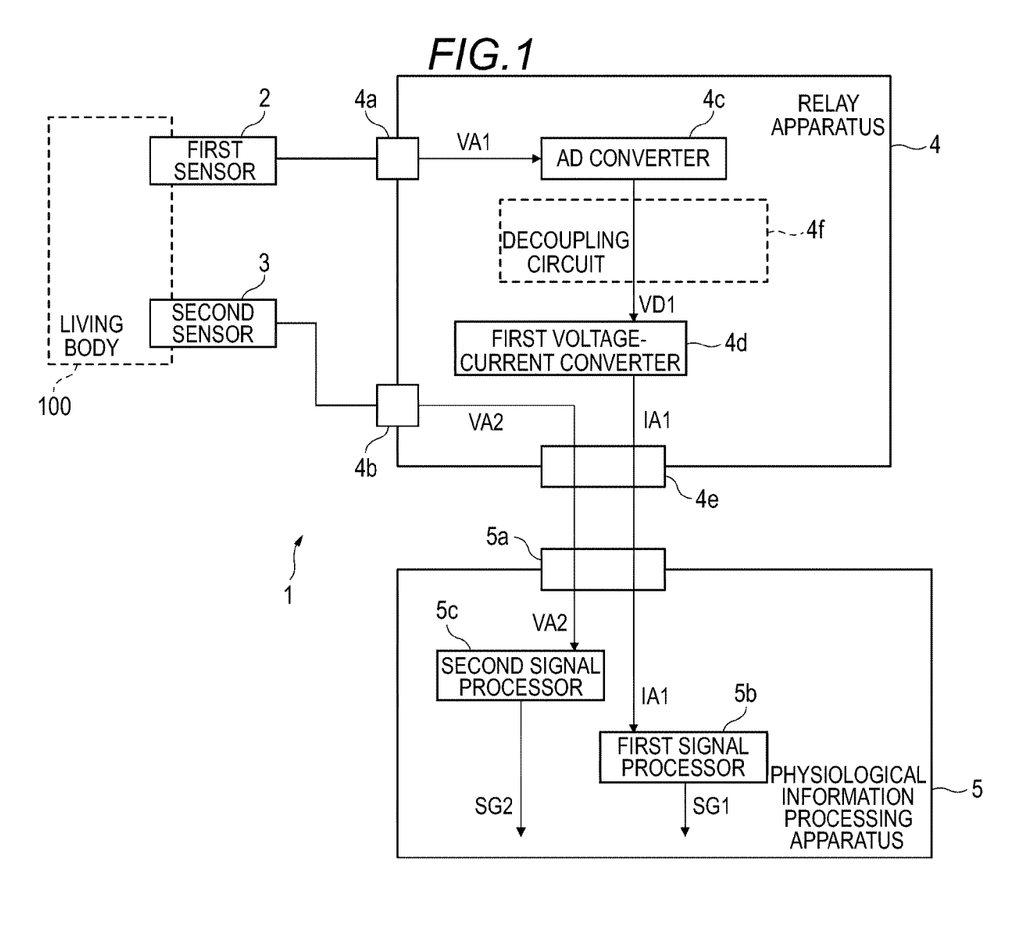
FIG. 1 illustrates a configuration of a physiological information processing system according to an exemplary embodiment of the presently disclosed subject matter.

FIG. 1 illustrates a configuration of a physiological information processing system 1 according to an exemplary embodiment of the presently disclosed subject matter. The physiological information processing system 1 is provided with a first sensor 2, a second sensor 3, a relay apparatus 4, and a physiological information processing apparatus 5.

The first sensor 2 is configured to be attachable to a living body 100. The first sensor 2 is configured to be able to output a first analog voltage signal VA1. Examples of the first sensor 2 include an SpO2 probe, an electrocardiogram sensor, an electroencephalogram sensor, etc.

When the first sensor 2 is an SpO2 probe, it includes a light-emitter and a light-detector. Light emitted from the light-emitter and transmitted through or reflected on living tissues (the tip of a finger, the tip of a toe, an ear lobe, etc. of a living body 100) is detected by the light-detector. A signal corresponding to the intensity of detected light changing in accordance with pulsation of a blood flow flowing through the living tissues is output as the first analog voltage signal VA1.

When the first sensor 2 is an electrocardiogram sensor or an electroencephalogram sensor, it includes electrodes. The electrodes are attached to certain locations on the living body 100 to detect a bioelectric potential in that place. A signal corresponding to the bioelectric potential is output as the first analog voltage signal VA1.

The second sensor 3 is configured to be attachable to the living body 100. The second sensor 3 is configured to be able to output a second analog voltage signal VA2. Examples of the second sensor 3 include an SpO2 probe, an electrocardiogram sensor, an electroencephalogram sensor, etc. Since configurations of the examples of the second sensor 3 are the same as those of the first sensor 2, repetitive description about the configurations of the examples will be omitted.

The relay apparatus 4 can include a first input connector 4a, a second input connector 4b, an analog-to-digital converter 4c, a first voltage-to-current converter 4d, and a first interface connector 4e.

The first input connector 4a is configured to be able to be connected to the first sensor 2. The second input connector 4b is configured to be able to be connected to the second sensor 3.

The analog-to-digital converter 4c is configured to convert the first analog voltage signal VA1 into a first digital voltage signal VD1 upon receipt of the first analog voltage signal VA1 from the first sensor 2 through the first input connector 4a. The analog-to-digital converter 4c may be configured to also perform various signal processings which can be made when the first analog voltage signal VA1 is converted into the first digital voltage signal VD1.

The first voltage-to-current converter 4d is configured to convert the first digital voltage signal VD1 into a first analog current signal IA1. For example, the first voltage-to-current converter 4d is configured as a low-pass filter which limits a bandwidth to pass a fundamental frequency and a third harmonic frequency of a pulse signal while attenuating fifth and higher harmonic frequencies of the pulse signal.

The first interface connector 4e is a single connector. The first interface connector 4e is configured to be able to output the first analog current signal IA1 output from the first voltage-to-current converter 4d, and the second analog voltage signal VA2 received from the second sensor 3 through the second input connector 4b. That is, a signal terminal that outputs the first analog current signal IA1 and a signal terminal that outputs the second analog voltage signal VA2 are disposed inside a housing of the single connector.

For example, the physiological information processing apparatus 5 is a bedside monitor or a pulse photometer. The physiological information processing apparatus 5 can include a second interface connector 5a, a first signal processor 5b and a second signal processor 5c.

The second interface connector 5a is a single connector. The second interface connector 5a is configured to be able to receive the first analog current signal IA1 and the second analog voltage signal VA2 both of which are output from the first interface connector 4e. That is, a signal terminal receiving the first analog current signal IA1 and a signal terminal receiving the second analog voltage signal VA2 are disposed inside a housing of the single connector.

The first signal processor 5b is configured to convert the first analog current signal IA1 into a first physiological information signal SG1 upon receipt of the first analog current signal IA1 through the second interface connector 5a. The first physiological information signal SG1 is a signal by which physiological information detected through the first sensor 2 can be presented to a user. The presentation to the user can be performed in a visual manner, in an audible manner or in a combined manner of the both.

For example, when the first sensor 2 is an SpO2 probe, the first physiological information signal SG1 is a signal by which arterial oxygen saturation or a heart rate of the living body 100 can be presented to the user. When the first sensor 2 is an electrocardiogram sensor or an electroencephalogram sensor, the first physiological information signal SG1 is a signal by which an electrocardiographic waveform or an electroencephalographic waveform of the living body 100 can be presented to the user. That is, the first signal processor 5b is configured to perform necessary arithmetic processing for obtaining the aforementioned first physiological information signal SG1 from the received first analog current signal IA1. Since the arithmetic processing per se is well known, detailed description thereof will be omitted.

The second signal processor 5c is configured to convert the second analog voltage signal VA2 into a second physiological information signal SG2 upon receipt of the second analog voltage signal VA2 through the second interface connector 5a. The second physiological information signal SG2 is a signal by which physiological information detected through the second sensor 3 can presented to the user. The presentation to the user can be performed in a visual manner, in an audible manner or in a combined manner of the both. Examples of the second physiological information signal SG2 are the same as those of the first physiological information signal SG1. The second physiological information signal SG2 is a digital voltage signal. That is, the second signal processor 5c is configured to apply analog-to-digital conversion to the received second analog voltage signal VA1 and to perform necessary arithmetic processing for obtaining the aforementioned second physiological information signal SG2. Since the arithmetic processing per se is well known, detailed description thereof will be omitted.

According to the configuration described above, the signal derived from the output of the first sensor 2 and the signal derived from the output of the second sensor 3 can be input to the physiological information processing apparatus 5 through the single second interface connector 5a. Here, the first analog voltage signal VA1 output from the first sensor 2 is converted into the first digital voltage signal VD1 by the analog-to-digital converter 4c and further converted into the first analog current signal IA1 by the first voltage-to-current converter 4d. Even in the configuration in which the signal derived from the output of the first sensor 2 and the signal derived from the output of the second sensor 3 pass through the same connectors (the first interface connector 4e and the second interface connector 5a), it is possible to avoid mixture of noise into a communication path because the two signals are analog signals. Thus, the terminals through which the signals derived from the sensors pass can be made close to each other or disposed efficiently. Thus, the degree of freedom in design can be increased so that the size of the second interface connector 5a can be reduced.

Further, since the first analog voltage signal VA1 is once converted into the first digital voltage signal VD1, the number of terminals required for communication can be reduced. That is, the number of terminals in the second interface connector 5a can be reduced in comparison with a configuration where a single connector is provided on the physiological information processing apparatus 5 side and the first analog voltage signal VA1 output from the first sensor 2 and the second analog voltage signal VA2 output from the second sensor 3 are input to the connector. Also in this manner, the size of the second interface connector 5a can be reduced.

Accordingly, it is possible to suppress an increase in the size or cost of the physiological information processing apparatus 5 while avoiding mixture of noise into signal communication.

The first signal processor 5b may include an analog-to-digital conversion function. That is, the first physiological information signal SG1 may be a digital voltage signal.

In this case, the first physiological information signal SG1 can be handled similarly to the second physiological information signal SG2 which is a digital voltage signal. Therefore, easiness or the degree of freedom of signal processing in a subsequent stage inside the physiological information processing apparatus 5 is improved.

The first voltage-to-current converter 4d may include at least one resistor device.

In this case, it is possible to suppress an increase in the size or cost of the physiological information processing apparatus 5 with a very simple and inexpensive configuration while avoiding mixture of noise into signal communication.

As shown in FIG. 1, the physiological information processing system 1 may further include a decoupling circuit 4f. The decoupling circuit 4f is provided between the analog-to-digital converter 4c and the first voltage-to-current converter 4d. The decoupling circuit 4f is provided for providing basic insulation against a current flowing unexpectedly from the physiological information processing apparatus 5 side. The decoupling circuit 4f may be achieved by a transformer or a photocoupler.

The decoupling circuit 4f is required only when the first sensor 2 is used. That is, the first sensor 2 is not always in use but a use form in which only the output of the second sensor 3 is input to the physiological information processing apparatus 5 is also possible. When the decoupling circuit 4f which is not always necessarily in use is provided inside the physiological information processing apparatus 5, the physiological information processing apparatus 5 will be increased in size and cost. On the other hand, when the decoupling circuit 4f is provided outside the physiological information processing apparatus 5 (inside the relay apparatus 4 in the exemplary embodiment described above), basic insulation can be provided while the physiological information processing apparatus 5 is suppressed from increasing in size and cost.

Figure 2A:
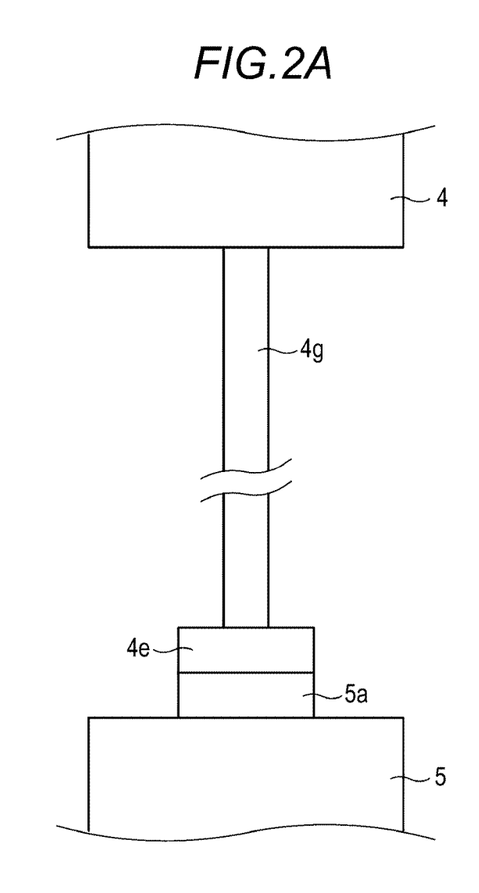
FIG. 2A illustrates an example of a connection between a relay apparatus and a physiological information processing apparatus in the physiological information processing system.
Figure 2B:
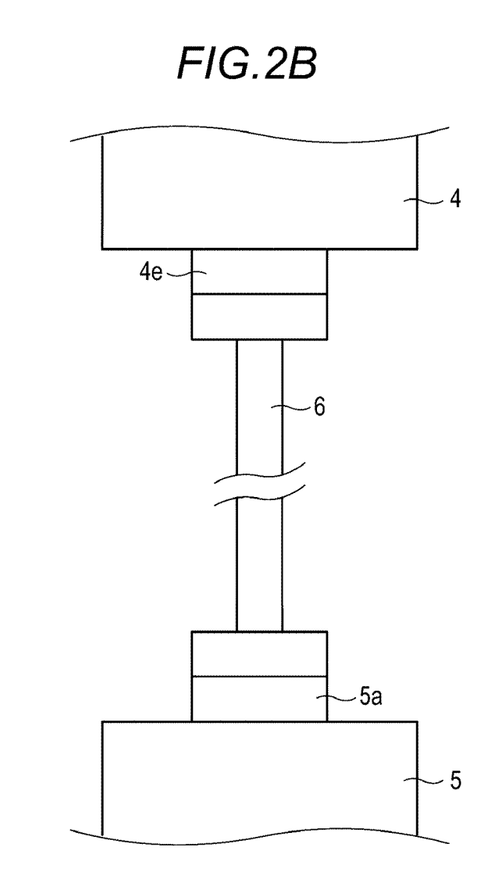
FIG. 2B illustrates another example of the connection between the relay apparatus and the physiological information processing apparatus.

FIGS. 2A and 2B illustrates examples of a connection between the first interface connector 4e and the second interface connector 5a.

As shown in FIG. 2A, the first interface connector 4e and the second interface connector 5a may be connected to each other directly. In this case, the first interface connector 4e is provided at a distal end of a cable 4g.

According to such a configuration, degradation of signal quality due to mixture of noise can be avoided while the first analog current signal IA1 derived from the output of the first sensor 2 and the second analog voltage signal VA2 derived from the output of the second sensor 3 are transmitted in parallel inside the same cable 4g. In addition, the degree of freedom in placement of the relay apparatus 4 and the physiological information processing apparatus 5 can be secured.

Alternatively, the first interface connector 4e and the second interface connector 5a may be connected communicably through a relay cable 6, as shown in FIG. 2B.

Figure 3:
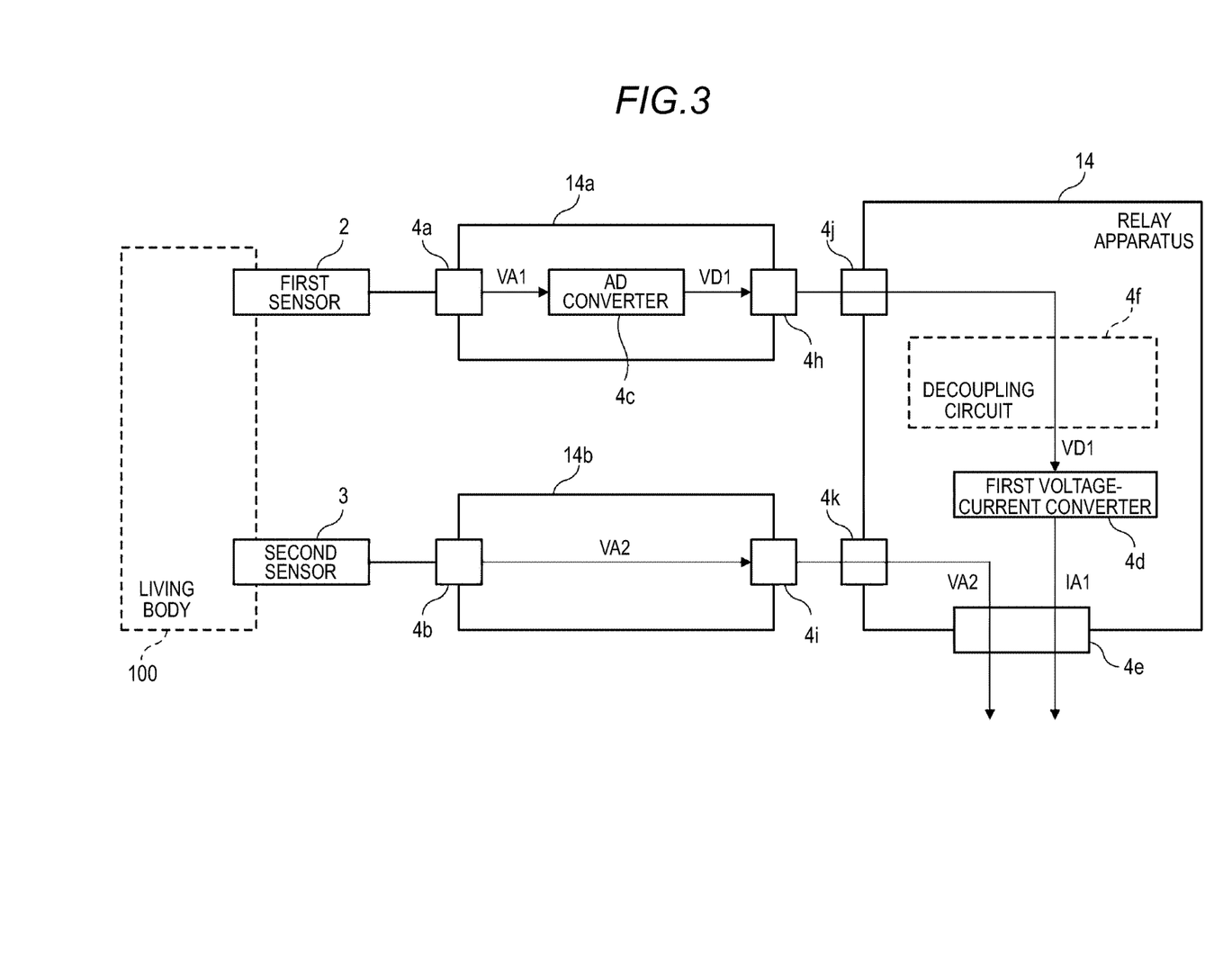
FIG. 3 illustrates another example of the relay apparatus.

FIG. 3 illustrates a relay apparatus 14 according to another example. The relay apparatus 14 corresponds to a relay apparatus in which parts of the function of the relay apparatus 4 shown in FIG. 1 are separated as a first relay cable 14a and a second relay cable 14b.

The first relay cable 14a can include the first input connector 4a and the analog-to-digital converter 4c. The first relay cable 14a can further include a first output connector 4h. The first output connector 4h is configured to be able to output a first digital voltage signal VD1.

The second relay cable 14b includes the aforementioned second input connector 4b. The second relay cable 14b further includes a second output connector 4i. The second output connector 4i is configured to be able to output a second analog voltage signal VA2.

The relay apparatus 14 (an example of a housing) can include a third input connector 4j and a fourth input connector 4k. The third input connector 4j is configured to be able to be connected to the first output connector 4h. The fourth input connector 4k is configured to be able to be connected to the second output connector 4i. The first voltage-to-current converter 4d and the decoupling circuit 4f are disposed inside the relay apparatus 14.

According to such a configuration, the size of the relay apparatus 14 can be reduced. In addition, the degree of freedom in placement of the relay apparatus 14 relative to the living body 100 to which the first sensor 2 and the second sensor 3 are attached is improved.

The relay apparatus 14 may not be provided with both the first relay cable 14a and the second relay cable 14b. One of the first relay cable 14a and the second relay cable 14b may be integrated into the relay apparatus 14. That is, at least one of the third input connector 4j and the fourth input connector 4k may be provided in accordance with presence/absence of the first output connector 4h and the second output connector 4i.

Figure 4:
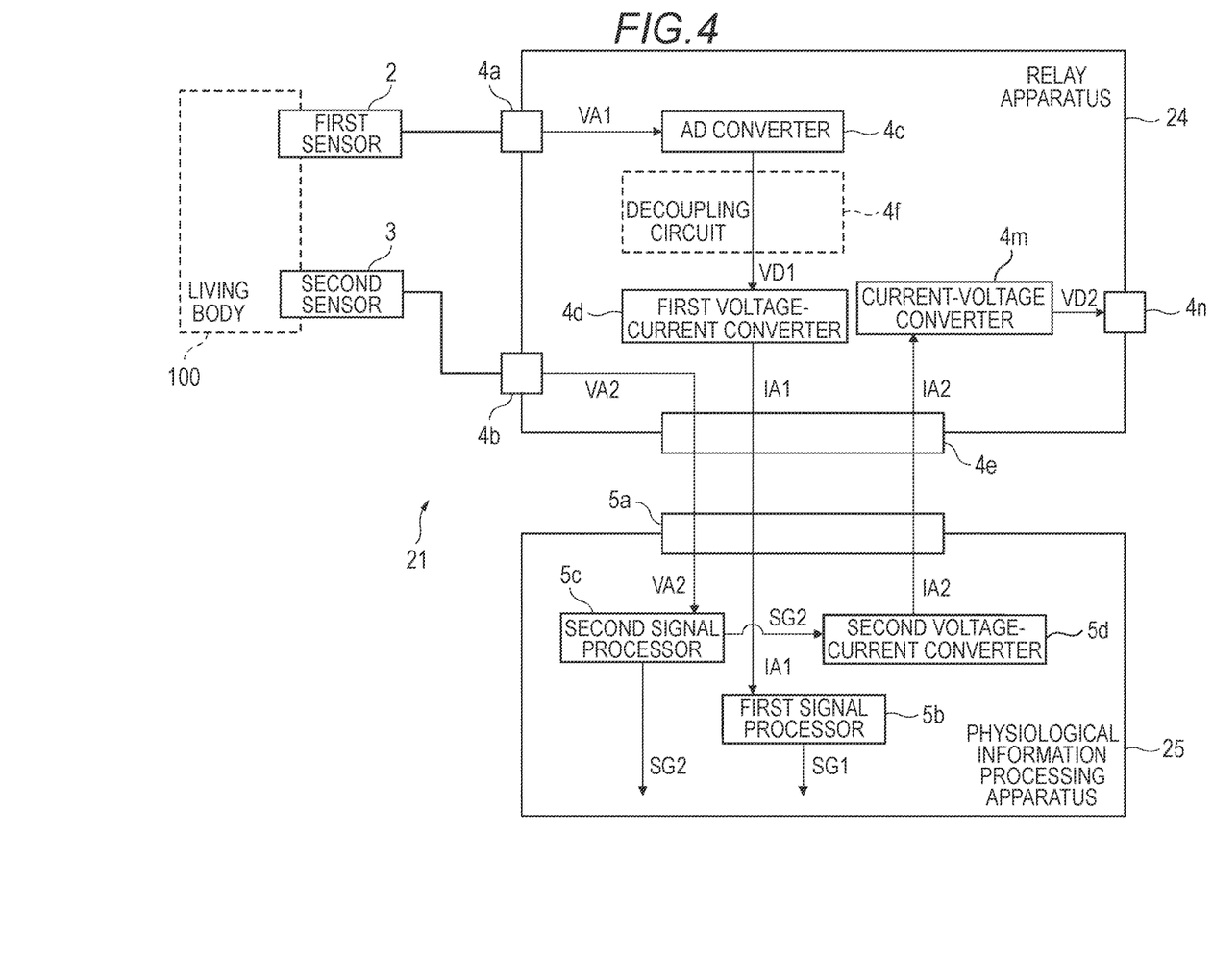
FIG. 4 illustrates a configuration of a physiological information processing system according to a second exemplary embodiment.

FIG. 4 illustrates a configuration of a physiological information processing system 21 according to another exemplary embodiment of the presently disclosed subject matter. Elements that are identical or equivalent to those of the physiological information processing system 1 will be denoted by the same reference signs, and repetitive description thereof will be omitted. The physiological information processing system 21 is provided with a relay apparatus 24 and a physiological information processing apparatus 25.

The physiological information processing apparatus 25 includes a second voltage-to-current converter 5d. The second voltage-to-current converter 5d is configured to convert a second physiological information signal SG2 output from a second signal processor 5c into a second analog current signal IA2. The second voltage-to-current converter 5d may be configured, for example, as a low-pass filter, same or similarly to a first voltage-to-current converter 4d. The second voltage-to-current converter 5d may be achieved by at least one resistor device. The second analog current signal IA2 is output from a second interface connector 5a.

The relay apparatus 24 includes a current-to-voltage converter 4m. The current-to-voltage converter 4m is configured to convert the second analog current signal IA2 into a second digital voltage signal VD2 upon receipt of the second analog current signal IA2 through a first interface connector 4e. Specifically, the current-to-voltage converter 4m includes a device (such as a high speed operational amplifier) which can follow a frequency band passed by the second voltage-to-current converter 5d. In this case, a cutoff frequency of the current-to-voltage converter 4m is determined to be not lower than a cutoff frequency of the second voltage-to-current converter 5d in the viewpoint of making filtering operation stable. Thus, noise in a signal line between the second voltage-to-current converter 5d and the current-to-voltage converter 4m can be suppressed.

The relay apparatus 24 includes an output terminal 4n. The output terminal 4n is configured to be able to output the second digital voltage signal VD2. The output terminal 4n is configured as a general-purpose data communication terminal such as a USB terminal.

According to such a configuration, it is possible to input the second digital voltage signal VD2 to a computer to thereby perform quality inspection etc. on the physiological information processing apparatus 5. Since the terminal for extracting such a signal can be integrated into the second interface connector 5a, it is possible to suppress a cost increase of the physiological information processing apparatus 5 as compared with a case in which an exclusive signal extracting port is provided independently. In addition, the second physiological information signal SG2 which is a digital voltage signal is converted into the second analog current signal IA2 by the second voltage-to-current converter 5d, and then fed for communication with the relay apparatus 24. Accordingly, mixture of noise into signal communication for obtaining the second digital voltage signal VD2 can be avoided.

The relay apparatus 24 may be configured such that a part of its function is separated as at least one of a first relay cable and a second relay cable, like the relay apparatus 14 illustrated in FIG. 3.

Figure 5:
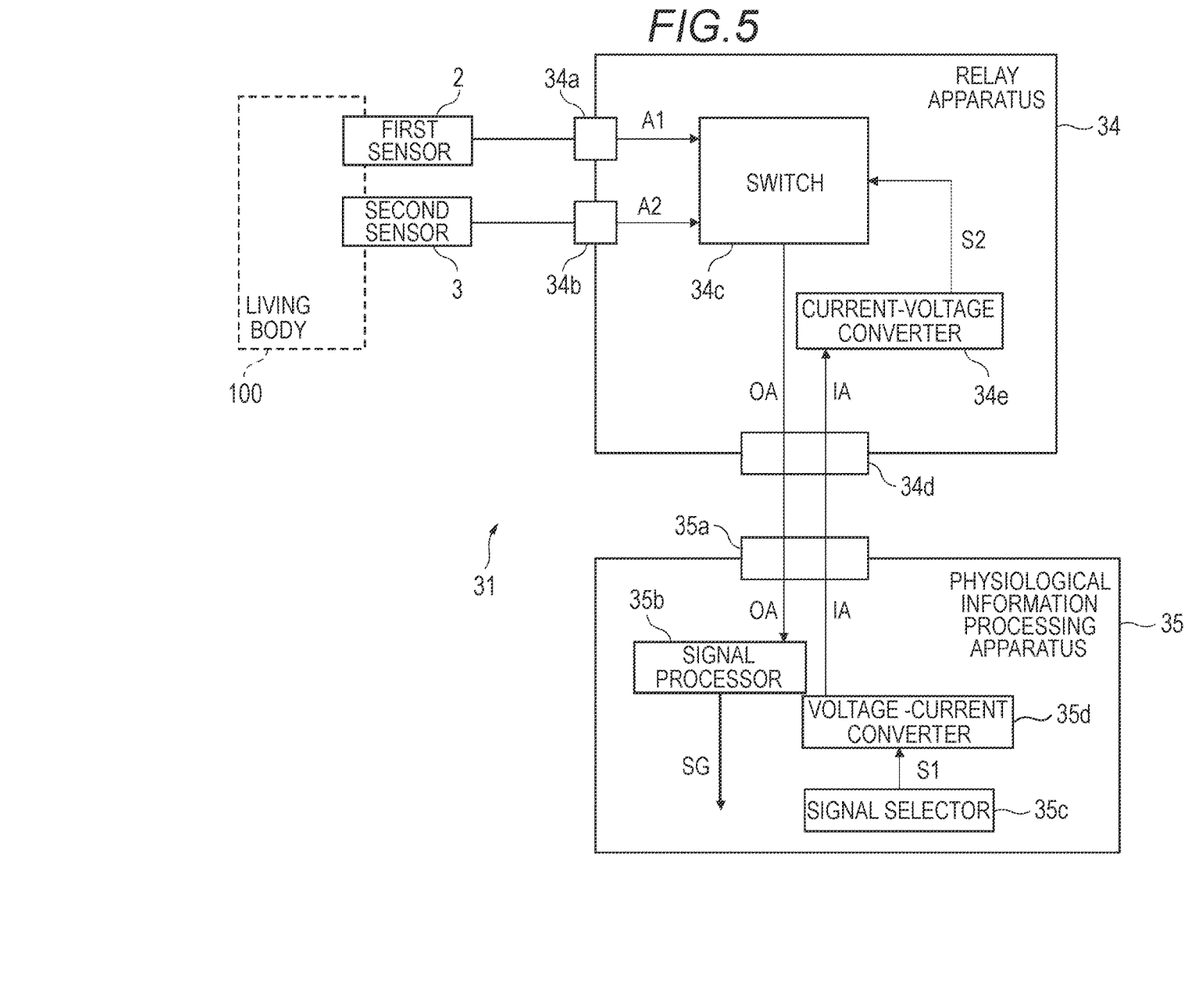
FIG. 5 illustrates a configuration of a physiological information processing system according to another exemplary embodiment of the presently disclosed subject matter.

FIG. 5 illustrates a configuration of a physiological information processing system 31 according to another exemplary embodiment of the presently disclosed subject matter. Elements that are identical or equivalent to those of the physiological information processing system 1 will be denoted by the same reference signs, and repetitive description thereof will be omitted. The physiological information processing system 31 includes a relay apparatus 34 and a physiological information processing apparatus 35.

The relay apparatus 34 includes a first input terminal 34a, a second input terminal 34b, a switch 34c, and a first interface connector 34d.

The first input terminal 34a is configured to receive a first signal A1 output from a first sensor 2. The first signal A1 is an analog signal.

The second input terminal 34b is configured to receive a second signal A2 output from a second sensor 3. The second signal A2 is an analog signal.

The switch 34c is configured to be able to output one of the first signal A1 and the second signal A2 as an analog output signal OA. The analog output signal OA is output from the replay apparatus 34 through the first interface connector 34d.

The physiological information processing apparatus 35 includes a second interface connector 35a, a signal processor 35b, a signal selector 35c and a voltage-to-current converter 35d.

The second interface connector 35a may be connected to the first interface connector 34d in any of the forms described with reference to FIGS. 2A and 2B. Accordingly, the analog output signal OA can be input to the physiological information processing apparatus 35 through the second interface connector 35a.

The signal processor 35b is configured to convert the analog output signal OA into a physiological information signal SG upon receipt of the analog output signal OA through the second interface connector 35a. The physiological information signal SG is a signal by which physiological information detected through the first sensor 2 or the second sensor 3 can be presented to a user. The presentation to the user may be performed in a visual manner, in an aural manner or in a combined manner of the both. Since arithmetic processing per se for obtaining such physiological information is well known, detailed description will be omitted.

The signal selector 35c is configured to output a first selection signal S1. The first selection signal S1 is a signal for selecting which output (the output from the first sensor 2 or the output from the second sensor 3) to be subjected to signal processing by the signal processor 35b. The first selection signal S1 is a digital voltage signal.

The voltage-to-current converter 35d is configured to convert the first selection signal S1 output from the signal selector 35c into an analog current signal IA, and then output the converted analog current signal IA from the second interface connector 35a. The voltage-to-current converter 35d is configured, for example, as a low-pass filter, similarly to the first voltage-to-current converter 4d. The voltage-to-current converter 35d may be achieved by at least one resistor device.

The analog current signal IA is input to the relay apparatus 34 through the first interface connector 34d. The relay apparatus 34 further includes a current-to-voltage converter 34e. The current-to-voltage converter 34e is configured to convert the analog current signal IA into a second selection signal S2 upon receipt of the analog current signal IA through the first interface connector 34d. The second selection signal S2 is a digital voltage signal. The current-to-voltage converter 34e may be achieved, for example, by a high speed operational amplifier, similarly to the current-to-voltage converter 4m.

The switch 34c is configured to select one of the first signal A1 and the second signal A2 based on the second selection signal S2. When the second selection signal S2 gives an instruction to select the first signal A1, the switch 34c outputs the first signal A1 as the analog output signal OA. In this case, the output of the first sensor 2 is fed to be subjected to signal processing by the signal processor 35b. When the second selection signal S2 gives an instruction to select the second signal A2, the switch 34c outputs the second signal A2 as the analog output signal OA. In this case, the output of the second sensor 3 is fed to be subjected to signal processing by the signal processor 35b.

According to the configuration described above, the signal derived from the output of the first sensor 2 and the signal derived from the output of the second sensor 3 can be selectively input to the physiological information processing apparatus 35 through the single second interface connector 35a. Thus, there is no need to provide a signal input connector for each sensor so that it is possible to suppress a cost increase of the physiological information processing apparatus 35.

In addition, the first selection signal S1 for performing signal selection is converted into the analog current signal IA by the voltage-to-current converter 35d, and then the converted analog current signal IA is output from the second interface connector 35a. Even in the configuration in which a signal for selecting a sensor to be subjected to signal processing, and an output signal from the sensor input as an acknowledge to the signal pass through the same connectors (the first interface connector 34d and the second interface connector 35a), it is possible to avoid mixture of noise into a communication path because both the signals are analog signals. Therefore, a terminal for outputting the signal for selecting the sensor can be integrated into the second interface connector 35a. Thus, it is possible to suppress a cost increase of the physiological information processing apparatus 35 as compared with a case in which a separate signal output port is provided independently. In addition, the terminal through which the selection signal passes and a terminal through which the output signal from the sensor passes can be made close to each other or arranged efficiently. Thus, the degree of freedom in design can be increased so that the size of the second interface connector 35a can be reduced.

Accordingly, it is possible to suppress an increase in the size or cost of the physiological information processing apparatus 35 while avoiding mixture of noise into signal communication.

The relay apparatus 34 may also be configured such that a part of its function is separated as at least one of a first relay cable and a second relay cable, like the relay apparatus 14 illustrated in FIG. 3.

Figure 6:
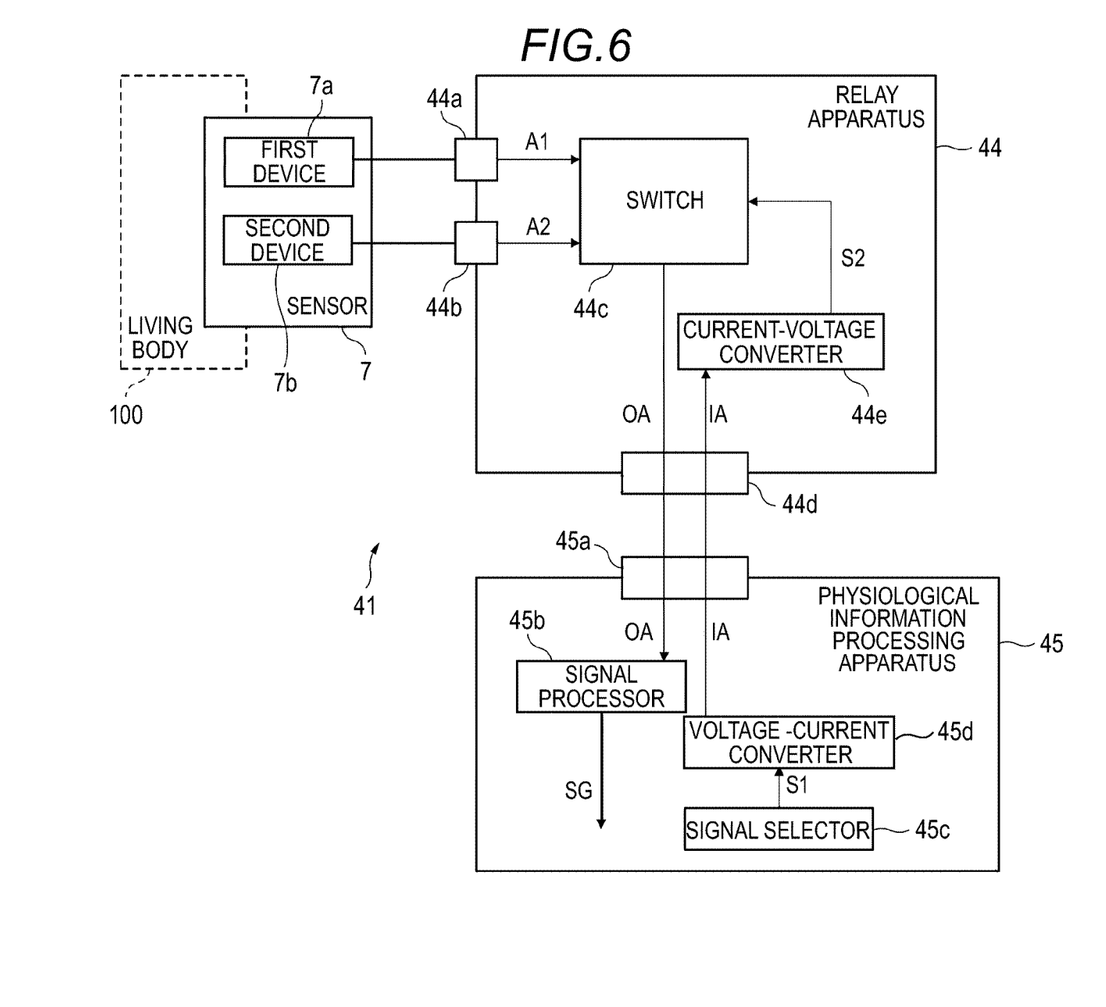
FIG. 6 illustrates a configuration of a physiological information processing system according to another exemplary embodiment of the presently disclosed subject matter.

FIG. 6 illustrates a configuration of a physiological information processing system 41 according to another exemplary embodiment of the presently disclosed subject matter. Elements that are identical or equivalent to those of the physiological information processing system 1 will be denoted by the same reference signs, and repetitive description thereof will be omitted. The physiological information processing system 41 includes a sensor 7, a relay apparatus 44, and a physiological information processing apparatus 45.

The sensor 7 includes a first element 7a and a second element 7b. The first element 7a and the second element 7b are configured to output different significant signals inside the same sensor. The first element 7a and the second element 7b may be provided to detect a same physiological parameter or to detect different physiological parameters. Examples of the first element 7a and the second element 7b include a plurality of light-detectors associated with different wavelengths in an SpO2 probe, a plurality of electrodes associated with different positions in a bioelectric potential gauge, etc.

The relay apparatus 44 can include a first input terminal 44a, a second input terminal 44b, a switch 44c, and a first interface connector 44d.

The first input terminal 44a is configured to receive a first signal A1 output from the first element 7a. The first signal A1 is an analog signal.

The second input terminal 44b is configured to receive a second signal A2 output from the second element 7b. The second signal A2 is an analog signal.

The switch 44c is configured to be able to output one of the first signal A1 and the second signal A2 as an analog output signal OA. The analog output signal OA is output from the replay apparatus 44 through the first interface connector 44d.

The physiological information processing apparatus 45 can include a second interface connector 45a, a signal processor 45b, a signal selector 45c, and a voltage-to-current converter 45d.

The second interface connector 45a may be connected to the first interface connector 44d by any of the forms described with reference to FIGS. 2A and 2B. Accordingly, the analog output signal OA can be input to the physiological information processing apparatus 45 through the second interface connector 45a.

The signal processor 45b is configured to convert the analog output signal OA into a physiological information signal SG upon receipt of the analog output signal OA through the second interface connector 45a. The physiological information signal SG is a signal by which physiological information detected through the first element 7a or the second element 7b can be presented to a user. The presentation to the user may be performed in a visual manner, in an aural manner or in a combined manner of the both. Since arithmetic processing per se for obtaining such physiological information is well known, detailed description thereof will be omitted.

The signal selector 45c is configured to output a first selection signal S1. The first selection signal S1 is a signal for selecting which output (the output from the first element 7a or the output from the second element 7b) to be subjected to signal processing by the signal processor 45b. The first selection signal S1 is a digital voltage signal.

The voltage-to-current converter 45d is configured to convert the first selection signal S1 output from the signal selector 45c into an analog current signal IA, and then output the converted analog current signal IA from the second interface connector 45a. The voltage-to-current converter 45d is configured, for example, as a low-pass filter, similarly to the first voltage-to-current converter 4d. The voltage-to-current converter 45d may be achieved by at least one resistor device.

The analog current signal IA is input to the relay apparatus 44 through the first interface connector 44d. The relay apparatus 44 further includes a current-to-voltage converter 44e. The current-to-voltage converter 44e is configured to convert the analog current signal IA into a second selection signal S2 upon receipt of the analog current signal IA through the first interface connector 44d. The second selection signal S2 is a digital voltage signal. The current-to-voltage converter 44e may be achieved, for example, by a high speed operational amplifier, similarly to the current-to-voltage converter 4m.

The switch 44c is configured to select one of the first signal A1 and the second signal A2 based on the second selection signal S2. When the second selection signal S2 gives an instruction to select the first signal A1, the switch 44c outputs the first signal A1 as the analog output signal OA. In this case, the output of the first element 7a is fed to be subjected to signal processing by the signal processor 45b. When the second selection signal S2 gives an instruction to select the second signal A2, the switch 44c outputs the second signal A2 as the analog output signal OA. In this case, the output of the second element 7b is fed to be subjected to signal processing by the signal processor 45b.

According to the configuration described above, the signal derived from the output of the first element 7a and the signal derived from the output of the second element 7b can be selectively input to the physiological information processing apparatus 45 through the single second interface connector 45a. Thus, there is no need to provide a signal input connector for each device that outputs a signal so that it is possible to suppress a cost increase of the physiological information processing apparatus 45.

In addition, the first selection signal S1 for performing signal selection is converted into the analog current signal IA by the voltage-to-current converter 45d, and then the converted analog current signal IA is output from the second interface connector 45a. Even in the configuration in which a signal for selecting a device to be subjected to signal processing, and an output signal from the device input as an acknowledge to the signal pass through the same connectors (the first interface connector 44d and the second interface connector 45a), it is possible to avoid mixture of noise into a communication path because both the signals are analog signals. Therefore, a terminal for outputting a signal for selecting a device can be integrated into the second interface connector 45a. Thus, it is possible to suppress a cost increase of the physiological information processing apparatus 45 as compared with a case in which a separate signal output port is provided independently. In addition, the terminal through which the selection signal passes and a terminal through which the output signal from the device passes can be made close to each other or arranged efficiently. Thus, the degree of freedom in design can be increased so that the size of the second interface connector 45a can be reduced.

Accordingly, it is possible to suppress an increase in the size or cost of the physiological information processing apparatus 45 while avoiding mixture of noise into signal communication.

The relay apparatus 44 may also be configured such that a part of its function is separated as at least one of a first relay cable and a second relay cable, like the relay apparatus 14 illustrated in FIG. 3.

Figure 7:
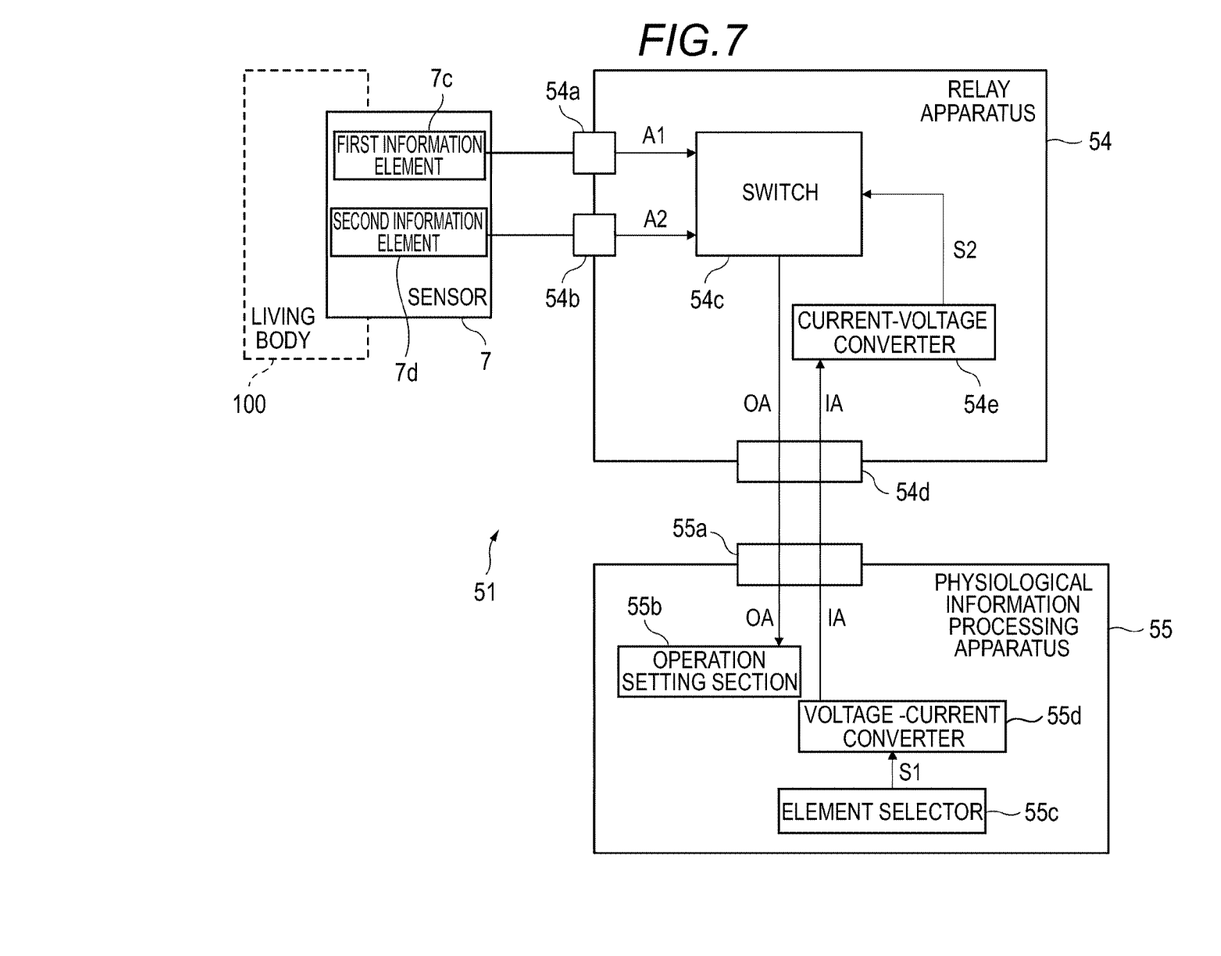
FIG. 7 illustrates a configuration of a physiological information processing system according to another exemplary embodiment of the presently disclosed subject matter.

FIG. 7 illustrates a configuration of a physiological information processing system 51 according to another exemplary embodiment of the presently disclosed subject matter. Elements that are identical or equivalent to those of the physiological information processing system 1 will be denoted by the same reference signs, and repetitive description thereof will be omitted. The physiological information processing system 51 is provided with a sensor 7, a relay apparatus 54, and a physiological information processing apparatus 55.

The sensor 7 can include a first information element 7c (an example of a first device) and a second information element 7d (an example of a second device). For example, the first information element 7c is an element indicating the type, an operating state, etc. of the first element 7a shown in FIG. 6. For example, the second information element 7d is an element indicating the type, an operating state, etc. of the second element 7b shown in FIG. 6. Examples of the first information element 7c and the second information element 7d can include values of resistor devices, values of capacitor devices, values of inductor devices, forward drop voltage values of diodes, shirt-circuited conductors, memories, atmospheric pressure sensors, temperature sensors, etc.

The relay apparatus 54 can include a first input terminal 54a, a second input terminal 54b, a switch 54c, and a first interface connector 54d.

The first input terminal 54a is configured to receive a first signal A1 output from the first information element 7c. The first signal A1 is an analog signal.

The second input terminal 54b is configured to receive a second signal A2 output from the second information element 7d. The second signal A2 is an analog signal.

The switch 54c is configured to be able to output one of the first signal A1 and the second signal A2 as an analog output signal OA. The analog output signal OA is output from the replay apparatus 54 through the first interface connector 54d.

The physiological information processing apparatus 55 can include a second interface connector 55a, an operation setting section 55b, an element selector 55c, and a voltage-to-current converter 55d.

The second interface connector 55a may be connected to the first interface connector 54d by any of the forms described with reference to FIGS. 2A and 2B. Accordingly, the analog output signal OA can be input to the physiological information processing apparatus 55 through the second interface connector 55a.

The operation setting section 55b is configured to set operation of the physiological information processing apparatus 55 based on the analog output signal OA input through the second interface connector 55a. The setting of the operation may be performed before or after detection operation performed by the sensor 7 or may be performed during the detection operation.

The element selector 55c is configured to output a first selection signal S1. The first selection signal S1 is a signal for selecting which element (the first information element 7c or the second information element 7d) to be referred to for the operation setting performed by the operation setting section 55b. The first selection signal S1 is a digital voltage signal.

The voltage-to-current converter 55d is configured to convert the first selection signal S1 output from the element selector 55c into an analog current signal IA, and then output the converted analog current signal IA from the second interface connector 55a. The voltage-to-current converter 55d is configured, for example, as a low-pass filter, same or similarly to the first voltage-to-current converter 4d. The voltage-to-current converter 55d may be achieved by at least one resistor device.

The analog current signal IA is input to the relay apparatus 54 through the first interface connector 54d. The relay apparatus 54 can further include a current-to-voltage converter 54e. The current-to-voltage converter 54e is configured to convert the analog current signal IA into a second selection signal S2 upon receipt of the analog current signal IA through the first interface connector 54d. The second selection signal S2 is a digital voltage signal. The current-to-voltage converter 54e may be achieved, for example, by a high speed operational amplifier, same or similarly to the current-to-voltage converter 4m.

The switch 54c is configured to select one of the first signal A1 and the second signal A2 based on the second selection signal S2. When the second selection signal S2 gives an instruction to select the first signal A1, the switch 54c outputs the first signal A1 as the analog output signal OA. In this case, the operation setting section 55b performs operation setting with reference to the first information element 7c. When the second selection signal S2 gives an instruction to select the second signal A2, the switch 54c outputs the second signal A2 as the analog output signal OA. In this case, the operation setting section 55b performs operation setting with reference to the second information element 7d.

According to the configuration described above, the signal derived from the output of the first information element 7c and the signal derived from the output of the second information element 7d can be selectively input to the physiological information processing apparatus 55 through the single second interface connector 55a. Thus, there is no need to provide a signal input connector for each information element so that it is possible to suppress a cost increase of the physiological information processing apparatus 55.

In addition, the first selection signal S1 for performing signal selection is converted into the analog current signal IA by the voltage-to-current converter 55d, and then the converted analog current signal IA is output from the second interface connector 55a. Even in the configuration in which a signal for selecting an information element to refer to, and an output signal from the information element input as an acknowledge to the signal pass through the same connectors (the first interface connector 54d and the second interface connector 55a), it is possible to avoid mixture of noise into a communication path because both the signals are analog signals. Therefore, a terminal for outputting a signal for selecting an information element can be integrated into the second interface connector 55a. Thus, it is possible to suppress a cost increase of the physiological information processing apparatus 55 as compared with a case in which a separate signal output port is provided independently. In addition, the terminal through which the selection signal passes and a terminal through which the output signal from the information element passes can be made close to each other or arranged efficiently. Thus, the degree of freedom in design can be increased so that the size of the second interface connector 55a can be reduced.

Accordingly, it is possible to suppress an increase in the size or cost of the physiological information processing apparatus 55 while avoiding mixture of noise into signal communication.

The relay apparatus 54 may also be configured such that a part of its function is separated as at least one of a first relay cable and a second relay cable, like the relay apparatus 14 illustrated in FIG. 3.

In the exemplary embodiment described above, the first information element 7c is associated with the first element 7a of the sensor 7 and the second information element 7d is associated with the second element 7b of the sensor 7. However, the first information element 7c and the second information element 7d may be associated with the same element, but in different forms.

The information elements may not be associated with the sensor 7. For example, the information elements may be associated with the first sensor 2, the second sensor 3, the relay apparatus 4, the relay apparatus 14, the first relay cable 14a, the second relay cable 14b, the relay apparatus 24, the relay apparatus 34, the relay apparatus 44, the relay apparatus 54, or a device provided in these apparatuses.

Figure 8:
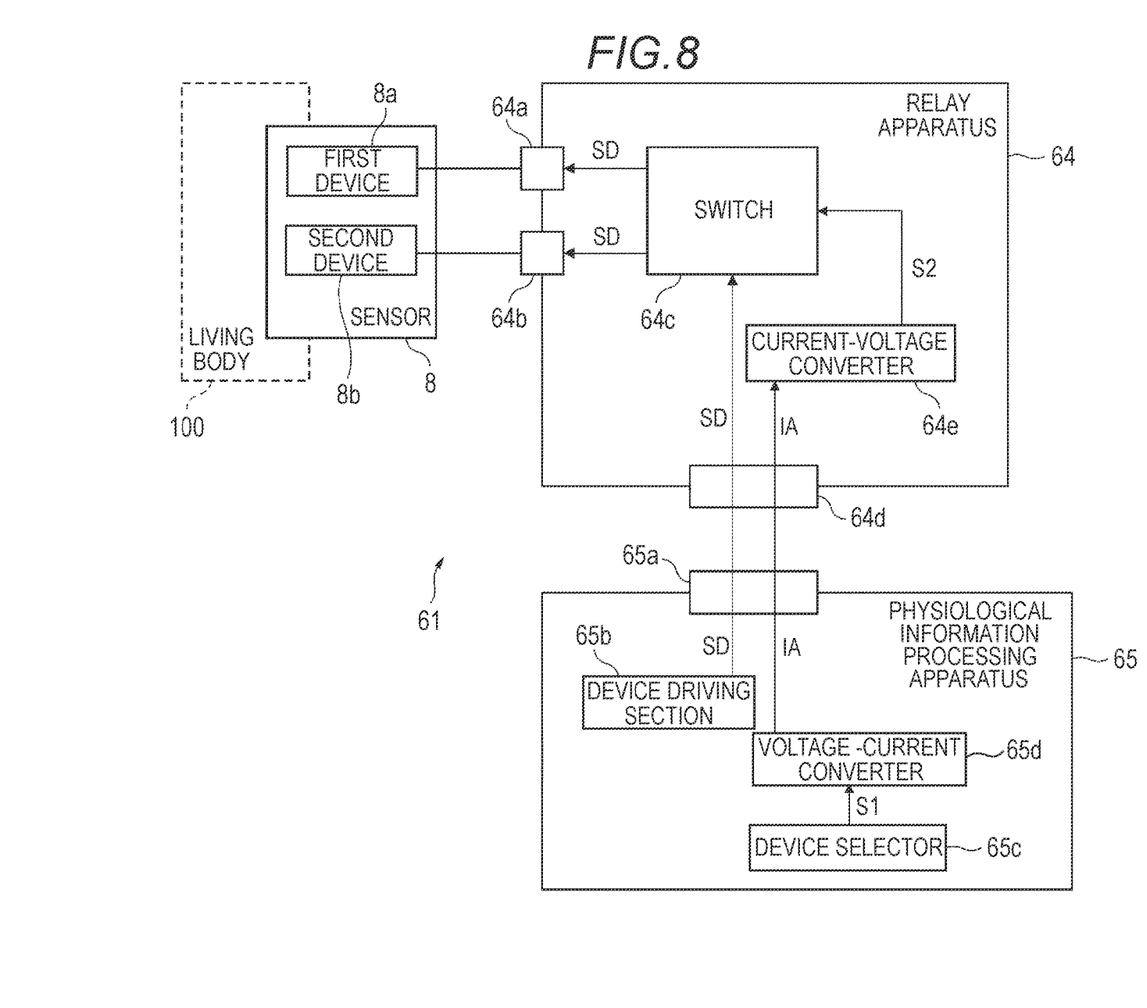
FIG. 8 illustrates a configuration of a physiological information processing system according to another exemplary embodiment of the presently disclosed subject matter.

FIG. 8 illustrates a configuration of a physiological information processing system 61 according to another exemplary embodiment of the presently disclosed subject matter. Elements that are identical or equivalent to those of the physiological information processing system 1 will be denoted by the same reference signs, and repetitive description thereof will be omitted. The physiological information processing system 61 is provided with a sensor 8, a relay apparatus 64, and a physiological information processing apparatus 65.

The sensor 8 includes a first element 8a and a second element 8b. The first element 8a and the second element 8b are devices performing different significant operations inside the same sensor. The first element 8a and the second element 8b may be provided to detect a same physiological parameter or to detect different physiological parameters. Examples of the first element 8a and the second element 8b include a plurality of light-emitters devices associated with different wavelengths in an SpO2 probe etc.

The physiological information processing apparatus 65 can include a first interface connector 65a, a device driving section 65b, a device selector 65c, and a voltage-to-current converter 65d.

The relay apparatus 64 can include a first output terminal 64a, a second output terminal 64b, a switch 64c, and a second interface connector 64d.

The first output terminal 64a is configured to be able to be electrically connected to the first element 8a. The second output terminal 64b is configured to be able to be electrically connected to the second element 8b.

The device driving section 65b is configured to output a device driving signal SD which can drive the first element 8a and the second element 8b, from the first interface connector 65a. The device driving signal SD is an analog signal.

The first interface connector 65a may be connected to the second interface connector 64d in any of the forms described with reference to FIGS. 2A and 2B. Accordingly, the device driving signal SD can be input to the relay apparatus 64 through the second interface connector 64d.

The switch 64c is configured to be able to output the device driving signal SD from one of the first output terminal 64a and the second output terminal 64b upon receipt of the device driving signal SD through the second interface connector 64d.

The device selector 65c is configured to output a first selection signal S1. The first selection signal S1 is a signal for selecting which terminal (the first output terminal 64a or the second output terminal 64b) the device driving signal SD is to be output from. The first selection signal S1 is a digital voltage signal.

The voltage-to-current converter 65d is configured to convert the first selection signal S1 output from the device selector 65c into an analog current signal IA, and then output the converted analog current signal IA from the first interface connector 65a. The voltage-to-current converter 65d is configured, for example, as a low-pass filter, similarly to the first voltage-to-current converter 4d. The voltage-to-current converter 65d may be achieved by at least one resistor device.

The analog current signal IA is input to the relay apparatus 64 through the second interface connector 64d. The relay apparatus 64 can further include a current-to-voltage converter 64e. The current-to-voltage converter 64e is configured to convert the analog current signal IA into a second selection signal S2 upon receipt of the analog current signal IA through the second interface connector 64d. The second selection signal S2 is a digital voltage signal. The current-to-voltage converter 64e may be achieved, for example, by a high speed operational amplifier, same or similarly to the current-to-voltage converter 4m.

The switch 64c is configured to select one of the first signal A1 and the second signal A2 based on the second selection signal S2. When the second selection signal S2 gives an instruction to select the first output terminal 64a, the switch 34c outputs the element driving signal SD from the first output terminal 64a. In this case, the first element 8a is driven by the device driving signal SD. When the second selection signal S2 gives an instruction to select the second output terminal 64b, the switch 64c outputs the device driving signal SD from the second output terminal 64b. In this case, the second element 8b is driven by the device driving signal SD.

According to the configuration described above, the signal for driving the first element 8a and the signal for driving the second element 8b can be output to the relay apparatus 64 through the single first interface connector 65a. Thus, there is no need to provided a signal output connector for each device to be driven so that it is possible to suppress a cost increase of the physiological information processing apparatus 65.

In addition, the first selection signal S1 for performing signal selection is converted into the analog current signal IA by the voltage-to-current converter 65d, and then the converted analog current signal IA is output from the first interface connector 65a. Even in the configuration in which a signal for selecting a device to be driven, and a signal for driving the selected device pass through the same connectors (the first interface connector 65a and the second interface connector 64d), it is possible to avoid mixture of noise into a communication path because both the signals are analog signals. Therefore, a terminal for outputting the signal for selecting the device can be integrated into the first interface connector 65a. Thus, it is possible to suppress a cost increase of the physiological information processing apparatus 65 as compared with a case in which a separate signal output port is provided independently. In addition, the terminal through which the selection signal passes and a terminal through which the output signal from the device passes can be made close to each other or arranged efficiently. Thus, the degree of freedom in design can be increased so that the size of the first interface connector 65a can be reduced.

Accordingly, it is possible to suppress an increase in the size or cost of the physiological information processing apparatus 65 while avoiding mixture of noise into signal communication.

The relay apparatus 64 may also be configured such that a part of its function is separated as at least one of a first relay cable and a second relay cable, like the relay apparatus 14 illustrated in FIG. 3.

In the exemplary embodiment described above, the single sensor 8 includes the first element 8a and the second element 8b. However, the first element 8a and the second element 8b may be provided in different sensors respectively.

While the presently disclosed subject matter has been described with reference to certain exemplary embodiments thereof, the scope of the presently disclosed subject matter is not limited to the exemplary embodiments described above, and it will be understood by those skilled in the art that various changes and modifications may be made therein without departing from the scope of the presently disclosed subject matter as defined by the appended claims.

What is claimed is:

1. A physiological information processing system comprising:
    a first input connector to which a first sensor to be attached to a living body is connected;
    a second input connector to which a second sensor to be attached to the living body is connected;
    an analog-to-digital converter configured to convert a first analog voltage signal into a first digital voltage signal, the first analog voltage signal being input from the first sensor through the first input connector;
    a first voltage-to-current converter configured to convert the first digital voltage signal into a first analog current signal;
    a first interface connector configured to output a second analog voltage signal and the first analog current signal, the second analog voltage signal being input from the second sensor through the second input connector;
    a physiological information processing apparatus comprising:
        a second interface connector through which the first analog current signal and the second analog voltage signal are input to the physiological information processing apparatus;
        a first signal processor to convert the first analog current signal into a first physiological information signal; and
        a second signal processor to convert the second analog voltage signal into a second physiological information signal, the second physiological information signal being a digital voltage signal.

2. The physiological information processing system according to claim 1, wherein the first physiological information signal is a digital voltage signal.

3. The physiological information processing system according to claim 1, wherein the first interface connector is provided at a distal end of a cable and is connected directly to the second interface conductor.

4. The physiological information processing system according to claim 1, wherein the first voltage-to-current converter comprises a resistor device.

5. The physiological information processing system according to claim 1, further comprising a decoupling circuit provided between the analog-to-digital converter and the first voltage-to-current converter.

6. The physiological information processing system according to claim 1, further comprising a housing on which at least one of a third input connector and a fourth input connector is provided,
wherein the first voltage-to-current converter is disposed inside the housing,
wherein the third input connector is connectable to a first output connector configured to output the first digital voltage signal, and
wherein the fourth input connector is connectable to a second output connector configured to output the second analog voltage signal.

7. The physiological information processing system according to claim 1, further comprising:
a second voltage-to-current converter provided inside the physiological information processing apparatus to convert the second physiological information signal into a second analog current signal to be output from the second interface connector;
a current-to-voltage converter configured to convert the second analog current signal into a second digital voltage signal, the second analog current signal being input from the first interface connector; and
an output terminal configured to output the second digital voltage signal.

8. A physiological information processing system comprising:
a first input terminal configured to receive a first signal, the first signal being an analog signal;
a second input terminal configured to receive a second signal, the second signal being an analog signal;
a switch configured to output one of the first signal and the second signal as an analog output signal;
a first interface connector configured to output the analog output signal;
a physiological information processing apparatus comprising:
a second interface connector through which the analog output signal is input to the physiological information processing apparatus;
a signal processor to convert the analog output signal into a physiological information signal;
a signal selector to output a first selection signal to select one of the first signal and the second signal, the first selection signal being a digital voltage signal;
a voltage-to-current converter to convert the first selection signal into an analog current signal and to output the analog current signal from the second interface connector; and
a current-to-voltage converter configured to convert the analog current signal into a second selection signal, the analog current signal being input through the first interface connector, and the second selection signal being a digital voltage signal,
wherein the switch selects one of the first signal and the second signal based on the second selection signal.

9. The physiological information processing system according to claim 8, wherein the first signal is an output signal from a first sensor attached to a living body, and the second signal is an output signal from a second sensor attached to the living body.

10. The physiological information processing system according to claim 8, wherein the first signal is an output signal from a first device of a sensor attached to a living body, and the second signal is an output signal from a second device of the sensor.

11. A physiological information processing system comprising:
a first output terminal configured to be electrically connected to a first device of a sensor attached to a living body;
a second output terminal configured to be electrically connected to a second device of the sensor;
a physiological information processing apparatus comprising a first interface connector;
a device driving section provided inside the physiological information processing apparatus to output a device driving signal from the first interface connector, the device driving signal being an analog signal that drives the first device and the second device;
a second interface connector configured to receive the device driving signal;
a switch configured to output the device driving signal from one of the first output terminal and the second output terminal, the device driving signal being input from the second interface connector;
a signal selector provided inside the physiological information processing apparatus to output a first selection signal, the selection signal being a digital voltage signal;
a voltage-to-current converter provided inside the physiological information processing apparatus to convert the first selection signal into an analog current signal and to output the analog current signal from the first interface connector; and
a current-to-voltage converter configured to convert the analog current signal into a second selection signal, the analog current signal being input through the second interface connector, and the second selection signal being a digital voltage signal,
wherein the switch selects one of the first output terminal and the second output terminal based on the second selection signal.

* * * * *

UNITED STATES PATENT AND TRADEMARK OFFICE
CERTIFICATE OF CORRECTION

PATENT NO. : 10,159,442 B2
APPLICATION NO. : 15/281290
DATED : December 25, 2018
INVENTOR(S) : Tetsuo Suzuki Page 1 of 1

It is certified that error appears in the above-identified patent and that said Letters Patent is hereby corrected as shown below:

On the Title Page

Column 1, item (30), please replace the Foreign Application Priority Data section as follows:
--Oct. 9, 2015 (JP)..................2015-200928--

Signed and Sealed this
Second Day of April, 2019

Andrei Iancu
*Director of the United States Patent and Trademark Office*